United States Patent [19]

Tiollais

[11] 4,371,625
[45] Feb. 1, 1983

[54] VECTORS FOR THE INSERTION THEREIN OF FOREIGN DNA FRAGMENTS, ACCORDING TO ANY TRANSLATION PHASE

[75] Inventor: Pierre Tiollais, Paris, France

[73] Assignees: Institut Pasteur; Inst. Nat'l de la Sante et Recherche, both of Paris, France

[21] Appl. No.: 93,270

[22] Filed: Nov. 13, 1979

[30] Foreign Application Priority Data

Nov. 13, 1978 [FR] France .............................. 78 32041

[51] Int. Cl.³ ...................... C12N 1/00; C12N 15/00
[52] U.S. Cl. .................................. 435/317; 435/172
[58] Field of Search ................ 435/172, 317; 536/27

[56] References Cited

PUBLICATIONS

Heyneker et al., Nature, vol. 263, pp. 748–752 (1976).
Scheller et al., Science, vol. 196, pp. 177–180 (1977).
O'Farrell et al., J. of Bact., vol. 134, pp. 645–654, May 1978.
Struhl, K., Cameron, J. R. and Davis, R. W. (1976) Proc. Natl. Acad. Sci. USA 73, 1471–1475.
Ratzkin, B. and Carbon, J. (1977) Proc. Natl. Acad. Sci. USA 74, 487–491.
Vapnek, D., Hautala, J. A., Jacobson, J. W., Giles, N. H. and Kushner, S. R. (1977) Proc. Natl. Acad. Sci. USA 74, 3508–3512.
Itakura, J., Hirose, T., Crea, R., Riggs, A. D., Heyneker, H. L., Bolivar, F. and Boyer, H. W. (1977) Science 198, 1056–1063.
Villa-Komaroff, L., Efstratiadis, A., Broome, S., Lomedico, P., Tizard, R., Naber, S. P., Chick, W. L. and Gilbert, W. (1978) Proc. Natl. Acad. Sci. USA 75, No. 8, 3727–3731.
Mercereau-Puijalon, O., Royal, A., Cami, B., Garapin, A., Krust, A., Gannon, F. and Kourlisky, Ph. (1978) Nature 275, 505–510.
Chow, L. T., Gelinas, R. E., Broker, T. R. and Roberts, R. J. (1977) Cell 12, 1–8.
Aloni, Y., Dhar, R., Laub, O., Horowitz, M. and Khoury, G. (1977) Proc. Natl. Acad. Sci. USA 74, 3686–3690.
Marx, J. L. (1977) Science 197, 853–923.
Jeffreys, A. J. and Flavell, R. A. (1977) Cell 12, 1097–1108.
Tiollais, P., Perricaudet, M., Pettersson, U. and Philipson, L. (1976) Gene 1, 49–63.
Barell, B. G. (1971) Proc. in Nucl. Acid Res. 2, 751–779.
Maxam, A. M. and Gilbert, W. (1977) Proc. Natl. Acad. Sci. USA 74, 560–564.
Adams, J. M., Jeppesen, P. G. N., Sanger, F. and Barrel, B. G. (1969) Nature 223, 1009–1014.
Sanger, F. and Coulson, A. R. (1975) J. Molec. Biol. 94, 441–448.
Bolivar, F., Rodriguez, R. L., Greene, P. J., Betlach, M. C., Heyneker, H. L., Boyer, H. W., Crossa, J. H. and Falkow, S. (1977) Gene 2, 95–113.
In vitro genetic recombinations, Scientific progress, 191, Nov.-Dec. 1977.
Moir, A. and Brammar, W. J. (1976) Molec. Gen. Genet. 149, 87–89.
Donoghue, D. J. and Sharp, P. A. (1976) Gene 1, 209–227.
Charney, Perricaudet, Galibert and Tiollais, (1978) Nucleic Acids Research, vol. 5, pp. 4479–4494.
Watson, J., Molecular Biology of the Gene.
Fowler, A. V. and Zabin, I., Proc. Natl. Acad. Sci., USA, 74, 1507–1510.

*Primary Examiner*—Alvin E. Tanenholtz
*Attorney, Agent, or Firm*—Weiser, Stapler & Spivak

[57] ABSTRACT

The invention pertains to a set of vectors (or of DNA fragments to be inserted in a vector) which distinguish from one another in that, taking into account one vector in which the number of pairs of bases between the reading initiation point of the vector and a point corresponding to the first pair of bases of a recognition site corresponding to a predetermined restriction enzyme, the two other vectors comprise between the corresponding points additional groups of pairs of bases comprising respectively two pairs of bases on the one hand and either one or four pairs of bases on the other hand, plus possibly whole numbers of triplets. On inserting a determined DNA fragment of which the expression is sought in bacteria in the three vectors, the reading of said DNA fragment will occur in phase as concerns one of the so modified vectors after transfection of bacteria therewith.

24 Claims, 15 Drawing Figures

Fig. 4.
Fig. 4a.
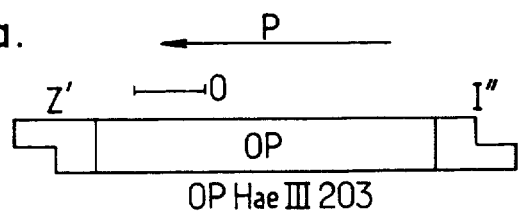
Fig. 4b.
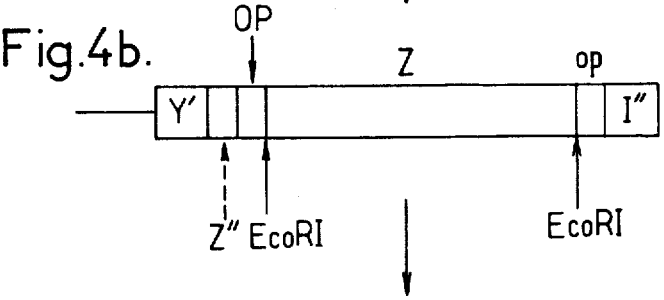
Fig. 4c.
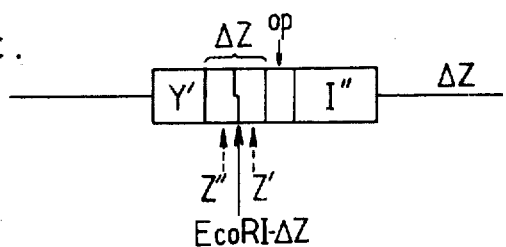
Fig. 4d.
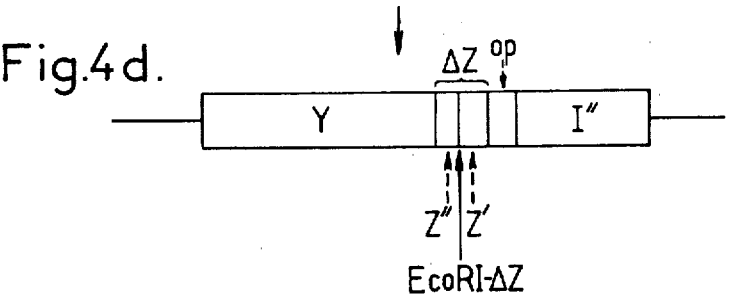

VECTORS FOR THE INSERTION THEREIN OF FOREIGN DNA FRAGMENTS, ACCORDING TO ANY TRANSLATION PHASE

The invention relates to modified vectors or groups of vectors, notably of the phage or plasmid type, in the genome of which may be inserted, by genetic fusion, preferably in vitro, a foreign DNA fragment capable of coding the production of a predetermined prokaryot or eukaryot protein, these phages being constructed so that they enable the expression in bacteria of this fragment (which may be any gene or other DNA, for instance that resulting from the enzymatic transcription of a messenger RNA).

It relates more particularly to vectors of this type which contain a fragment incorporated therein, said fragment including at least the promoter and at least a part of a gene which is associated therewith in said bacterial operon, said gene or part of gene comprising a specific site of recognition by a restriction enzyme, such as EcoRI, preferably to the exclusion of any other similar site in this same vector. Advantageously said fragment is derived from the lactose operon, said gene or part of gene then either comprising the Z gene or a portion of the latter. After in vitro opening of this vector by means of this restriction enzyme, it is possible to insert therein the abovesaid foreign DNA fragment, subject, if necessary, to the previous modification of its extremities to provide it with corresponding cohesive ends which then enable their mating, notably under the effect of a DNA-ligase, with the previously separated portions of the vector concerned.

It has been observed that the promoter of the bacterial operon, present or inserted in the vector was capable of providing a signal sufficient to enable the triggering of the expression into a bacterium into which this vector had previously been introduced, of the genes therein contained, including that of the foreign fragment, in the form of the production by the bacterium of a hybrid protein containing a polypeptide sequence corresponding to the portion of the gene of the bacterial operon (more particularly a sequence corresponding at least to the first amino-acids of the β-galactosidase in the case of the lactose operon) associated with the protein fragment coded by the foreign fragment. Thus it has been possible recently to induce the expression by a bacterium of some eukaryot genes, notably those of somatostatin, of pro-insulin and of chicken ovalbumin.

It must however be stressed that this operation can be carried out favorably only subject to a correct linking-up—in phase—of the gene of the bacterial operon and of the foreign DNA in the vector. It is known in fact that the coding of the successive amino-acids of a protein brings into play successive triplets of pairs of successive bases (codons) of DNA. It is thus necessary to ensure that the translation of the foreign DNA fragment, which then follows the previously initiated translation of the gene fragment of the bacterial operon, from their common junction point, is done according to the normal reading frame of the foreign gene, hence from codons corresponding effectively to the desired protein, rather than from those which are shifted either by one, or by two pairs of bases with respect to the normal initiation point of the translation of the foreign protein. This operation has been carried out with success in the case of the previously mentioned examples due to the knowledge previously acquired by the specialists, of the relative locations both of the fragment of the Z gene (which comprises notably the eight first triplets corresponding to the eight first amino-acids of the β-galactosidase) and of the gene coding the desired protein (particularly pro-insulin and ovalbumin) in certain of the vectors which have been used.

The realization of such linking up with other foreign DNA may however prove to be extremely delicate, even impossible with the same or other vectors. In this case, until now obviously still the most frequent, this difficulty can not even be appreciated exactly, failing precise knowledge either of the position in the DNA fragment of the gene coding the desired protein, or even the structure of the protein that this fragment is adapted to code in its cell of origin.

It is precisely an object of the invention to provide means which enable such difficulties to be overcome, notably vectors or groups of vectors that the user may put into practice to achieve suitable linking-up, if need be simultaneously, to determine rapidly which one in said group of vectors will ensure the correct translation of the foreign DNA previously incorporated in its genome.

The vector according to the invention which is derived from a pre-existing vector, as has been defined above, is characterized in that the location of the recognition site of the restriction enzyme concerned is shifted with respect to that of this same site in the pre-existing vector, or again with respect to the initiation site of the translation of the gene or fragment of gene associated with its promoter, through a group formed of either two pairs, of bases or of either one or two pairs of bases, if necessary associated with an additional whole multiple of supplementary triplets, it being possible for the pairs of bases of this group to be any possible one, however to the exclusion of those which, in the order in which they would be placed, would form at least one "nonsense" codon, that is to say one of the three codons among the sixty-four possible, which have been endowed by the genetic code with the function of causing the interruption of the translation.

Preferred vectors according to the invention are those in which the promoter is that of the lactose operon and the gene or part of gene which is associated therewith is constituted by the Z gene or a fragment of this Z gene, such as that which is adapted to code the eight first aminoacids of β-galactosidase, the restriction site concerned then being preferably an EcoRI site.

The shifts may also be expressed with respect to a fixed point in the vector concerned, advantageously that corresponding to the initiation point of the translation. Starting consequently from a vector in which the first pair of bases of the site of the restriction enzyme is separated from this initiation point by a whole number of triplets corresponding to the first amino-acids of the protein or part of protein coded for by said gene or part of gene (such as the Z gene or the eight first triplets of the latter) the two other vectors as defined distinguish over the preceding one by a shift of said site of recognition by the restriction enzyme with respect to the initiation point of the translation, said shift being caused by the insertion therebetween of two pairs of bases, on the one hand, of either one or four pairs of bases on the other hand and possibly in each case of additional associated whole multiples of supplementary triplets, whereby the inserted groups shall of course meet the condition expressed above as regards the avoidance of the formation of possible nonsense codons. Preferably, these insertions are effected in immediate proximity to the first pair of bases of said recognition site.

The invention also relates to the groups or sets of vectors which can thus be constituted and notably presented in the form of sets or kits of three vectors, essentially distinguished from one another in that, one of these vectors being characterized by the fact that the first pair of bases of its site of recognition by the restriction enzyme occurs at a distance from the initiation point of the translation corresponding to a whole multiple of triplets, the first pairs of bases of the said recognition sites of the two other vectors are respectively shifted with respect to the same initiation point by a distance corresponding to a whole number of triplets to which are added two pairs of bases and either one or four pairs of bases respectively (whereby said whole numbers may be zero).

Advantageously, these three vectors include respectively distinct mutation enabling their rapid recognition in genetic recombination operations which bring all three of them into play.

The invention thus makes available means enabling the specialist to carry out effectively genetic recombinations, notably in vitro, capable of providing the recombinants in which the inserted foreign fragment will then be expressed according to the correct reading frame by the bacteria previously transformed with such vectors.

More particularly, the invention is applicable in each of the following alternatives. The invention enables the choice of the suitable vector in the case where the primary sequence of the gene to be inserted is known, so that it suffices to select that of the three vectors which will enable, on the occasion of the translation, the reading phase of the inserted gene to be respected. On the contrary, in the case where the initial structure of the gene to be inserted is not known, said gene will be inserted in the three vectors concerned. That of these three vectors which will enable the complete expression of the inserted gene will then constitute the suitable vector for the correct reading phase of this gene. In fact, it is in all probability likely that the erroneous expressions obtained through two other vectors will be manifested generally by the production of proteins of much lower molecular weights, in any case having different biological properties. In fact, it can then be assumed that the translation will mostly be interrupted due to the presence of a then formed "nonsense" codon (statistically on the average three in sixty-four codons) as a result of an erroneous reading, itself caused by an out-of-phase linking-up of the foreign gene sought to be expressed to the corresponding gene part of the bacterial operon of the vector.

The invention relates also to the DNA fragments hereinafter called "insertion fragments", suitable for the production of vectors of the above-defined type including at least a promoter and a part of the gene or of one of the genes which is associated therewith in the corresponding bacterial operon, these fragments being characterized in that two of these fragments distinguish from a third one by a shift of their cohesive ends with respect to the initiation point of the reading of the corresponding gene or part of gene bringing into play distances corresponding respectively to groups, on the one hand, of two pairs of bases and, on the other hand, of either one or four pairs of bases, if necessary completed in each case by whole multiples of supplementary triplets, it being possible for the pairs of bases of these groups to be anyone, however to the exclusion of those which, in the order in which they are placed, would form at least one "nonsense" codon.

As in the case of the vectors, the promoter and the associated corresponding gene are preferably respectively the promoter and the Z gene of the lactose operon, the cohesive end concerned being an EcoRI cohesive end.

The invention relates also to a process for preparing from an insertion fragment including at least one cohesive end corresponding to a predetermined restriction enzyme, another fragment whose constitution results, after insertion in the same vector, in a shift of a phase at the level of its expression in a bacterium, which comprises trimming the projecting fragment which forms one of the strands of DNA at the level of said cohesive end, recombining notably by means of a suitable endonuclease the thus modified fragment, at the level of the free end formed, with another DNA fragment having a recognition site for this same restriction enzyme and including also a free end, the latter being separated from the first pair of bases taking part in the recognition site by a number of pairs of bases corresponding to the sum of either two pairs of bases or one or four pairs of bases and, if necessary, of a whole multiple of supplementary triplets, and finally treating the insertion fragment thus obtained with the same restriction enzyme, in order to reform the cohesive end concerned.

It is self-evident that it is possible also to form an insertion fragment whose use will lead to the third possibility of possible reading of the vector modified by bacteria, by repeating all these operations once more.

Such an "other fragment" as hereabove defined consists for example of a short fragment called hereafter a "linker" of the formula p5'GGAATTCC
CCTTAAGG5'p in which A represents adenine, T thymine, C cytosine and G guanine.

The insertions of the three fragments with shifted phases thus obtained in a phage or in a plasmid, and then the supplementary insertion of a foreign DNA fragment in the three types of vectors so obtained, lead to vectors capable of leading to translations dephased with respect to one another of the foreign fragments that they respectively include. The reading frames corresponding to these three phases may notably be illustrated as follows, at the level of the nucleotides taking part in the EcoRI recognition sites of such vectors

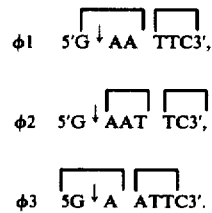

It is self-evident that this is only one example of a fragment which can be used for operations of this type.

The insertion fragments obtained can then be inserted in vectors, phages or plasmids, by any technique known in itself.

Other characteristics of the invention will appear also in the course of the description which follows of examples of the preparation of insertion fragments and preferred vectors utilizing the characteristics of the invention.

Reference will be made of the drawings in which:

FIG. 4 is a diagrammatic representation of the preparation of an insertion fragment in accordance with a preferred embodiment of the invention.

Figure 1:
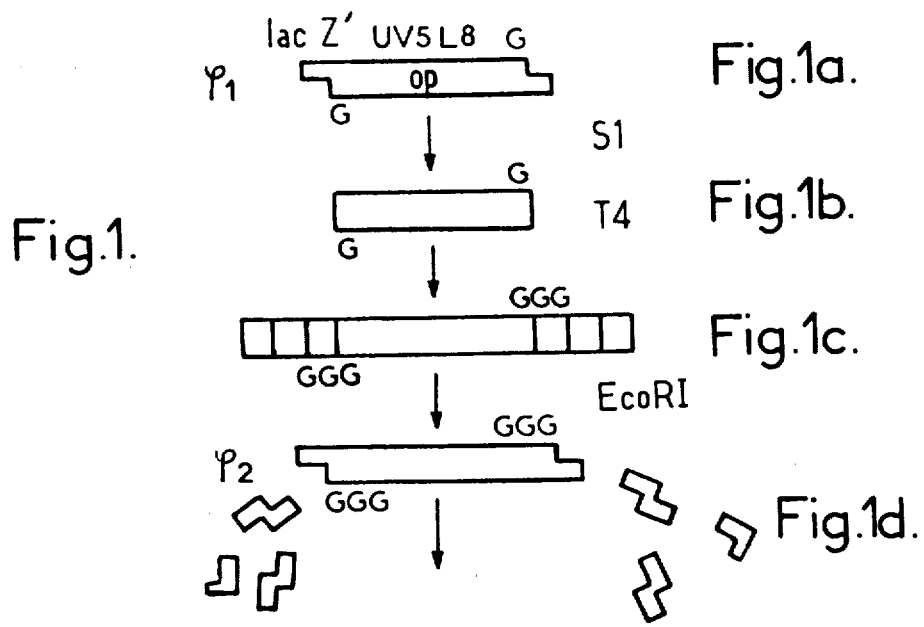
FIG. 1 is a diagram illustrating the process according to the invention.

The numbers between parentheses in the description which follows, refer to the bibliography at the end of the description.

MATERIALS AND METHODS

Bacterial strains and bacteriophages

All the bacterial strains used were derived from the strains E. coli K12: It was a MM294 strain which carries the plasmid pOP203 (UV5) C.N.C.M. No. I-066; the strain C600 recBC rk− mk− C.N.C.M. No. I-067; the strains YMC (SupF) C.N.C.M. No. I-068 and 3000X74 (lac sup°) C.N.C.M. No. I-069; phage λZQS-EcoRI (C.N.C.M. No. I-055).

Chemical Products

The following chemical products were used: Xgal=5-bromo-4-chloro-3-indolyl-β-D galactoside (Bachem). Melibiose (Baker). Agarose (Sigma). Acrylamide (Serva). 32P γ ATP (New England Nuclear). Octadeoxyribonucleotide 5′-OH-GGAATTCC-OH-3′ (Collaboration Research). Dimethyl-sulphate (Aldrich Chemical). Hydrazine (Eastman Organic Chemicals). Piperidine (BDH Biochemicals).

Enzymatic Reactions

The hydrolyses by HindIII endonuclease (Biolabs) were done in a Tris HCl: 6.6 mM, pH 7.5, mgCl2: 6.6 mM, β-mercaptoethanol: 6.6 mM, NaCl: 6 mM buffer. The hydrolyses by the HpaII and AluI endonucleases were done in a Tris HCl: 6.6 mM, pH 7.5, mgCl2: 6.6 mM, β-mercaptoethanol: 6.6 mM, NaCl: 6.6 mM buffer. The hydrolyses by the EcoRI endonuclease and the binding of the cohesive ends by the ligase polynucleotide of T4 have been described previously (12). The alkaline phosphatase (PL Laboratories), the DNase I purified by electrophoresis (Worthington) and the snake venom phosphodiesterase (Worthington) were used in the Tris HCl: 10 mM, pH 8.5, MgCl2: 10 mM buffer (13). The phosphorylation reaction at the 5′ position with 32P γ ATP by the kinase polynucleotide (PL Laboratories) was done as described by Maxam and Gilbert (14). The hydrolysis by S1 endonuclease was done in the NaCOOCH3: 25 mM, pH 4.5, ZnSO4: 1 mM, NaCl; 125 mM buffer for 1 hour at 25° C. The appropriate amount of enzyme was determined by analysis of the 5′ terminal nucleotide end of the EcoRI 203 fragment treated with increasing amounts of enzyme.

Binding of the free ends of octadeoxyribonucleotides (EcoRI linkers) to the DNA fragments 1 μg of "EcoRI linker" was marked at the 5′ phosphate end with 25 μCi of 32P γATP (specific activity 3 mCi/mM) by means of 2 units of kinase polynucleotide in 150 μl of Tris HCl: 50 mM, pH 9.5, MgCl2: 10 mM, DTT: 5 mM buffer for 1 hour at 37° C. After the addition of 0.03 mM of ATP, 2 units of kinase polynucleotide were added and incubation was continued again for 1 hour at 37° C. The mixture was lyophilized and the solid residue dissolved in 20 μl of Tris HCl: 6.6 mM, pH 7.6, MgCl2: 6.6 mM, ATP: 1 mM, DDT: 10 mM buffer which contained about 10 ng of EcoRI 203 (UV5) DNA fragments previously treated with S1 endonuclease. After the addition of 10 units of polynucleotide ligase of T4, the mixture was incubated for 48 hours at 14° C.

Other techniques

Analytical and preparative electrophoreses on gel were done according to Adams (15). The elution of the DNA fragments was effected as described by Maxam and Gilbert (14). Electrophoreses on 3 MM paper at pH 3.5 was done as described by Barell (13). The sequence of the DNA was constructed as described by Maxam and Gilbert (14). The filtration on Sephadex G100 was effected according to Sanger (16) in Corining serological pipettes of 1 ml. The multiplication of the bacteriophages and the genetic crossings were effected in the YMC bacterial strain, the purification of bacterial phages, the transfection in E. coli C600 rk− mk− recBC. The electrophoreses were done on agarose gels. Xgal, tetracycline and ampicillin were used in a solid L medium respectively at the following concentrations: 40 mg/liter, 15 mg/liter and 100 mg/liter.

Confinement

The experiments were carried out under the conditions L1 (P1) and B1 (EK1).

RESULTS

Chemical modifications of the ends of the fragment of DNA EcoRI 203 (UV5) (FIG. 1)

The process for the addition of two pairs of bases to each end of the DNA EcoRI 203 (UV5) fragment was as follows:

(1) Treatment of a lac Z′ UV5L8G fragment (FIG. 1a) with S1 endonuclease so as to produce free ends possessing G                        (FIG. 1b)
   C5′P;

(FIG. 1b);

(2) Ligation by T4 DNA ligase (T4 in FIG. 1) of the "linker"

EcoRI P5′GGAATTCC    to the end of the DNA fragment;
            CCTTAAGG5′P to the end of the DNA fragment;

(3) digestion of the new DNA fragment (shown diagrammatically in FIG. 1c) by EcoRI endonuclease, which generates a DNA fragment possessing two supplementary pairs of bases

GG
   CC at each EcoRI end (FIG. 1d). The latter DNA fragment is called EcoRI 207 (UV5) fragment. The DNA EcoRI 211 (UV5) fragment was constructed by the same process.

125 μg of pOP203 plasmid which carries the EcoRI 203 (UV5) fragment were hydrolysed by EcoRI endonuclease. The DNA was then treated with S1 endonuclease. After labeling the 5' end with ATP γ 32P using the kinase polynucleotide, the EcoRI 203 (UV5) fragment was prepared by electrophoresis in an 8% polyacrylamide gel. To test the efficiency of the S1 endonuclease, an aliquot of DNA was used to determine the nature of the 5' nucleotide terminal. It was as expected essentially constituted by cytosine.

The EcoRI linkers were ligated or bound to the DNA fragment (see Materials and Methods). The electrophoretic analysis of the aliquots sampled before and after the EcoRI treatment, showed that the linkers were attached to the DNA fragment. The DNA fragment digested by EcoRI was separated from the linkers by chromatography on a SEPHADEX G100 column. The fragment was eluted in a total volume of 100 μl.

A portion of the fragment of modified DNA, in 15 μl, was then bound in vitro to the pBR322 (17) plasmid digested with EcoRI. This DNA was used to convert the bacterial strain MM294. About 8% of the colonies were blue on the L Xgal, tetracycline medium, which indicated that they carried the pBR322 plasmid with the lac operator.

Analysis of the lac Z end of the fragment of EcoRI 207 (UV5) DNA

Starting from blue colonies described in the previous section, four clones were amplified and the structure of their plasmids (pPC21, pPC22, pPC23, and pPC24), was analysed. The treatment of each plasmid by a EcoRI endonuclease produced a DNA fragment whose electrophoretic mobility (in an 8% acrylamide gel) was slightly less than that of the initial EcoRI 203 (UV5) fragment. This band corresponds to the EcoRI 207 (UV5) fragment.

Figure 2:
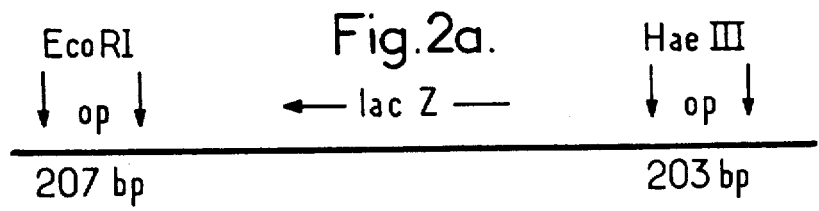
FIG. 2 is a diagram illustrating the main steps of the recombination of such an insertion fragment with a vector.
Figure 2:
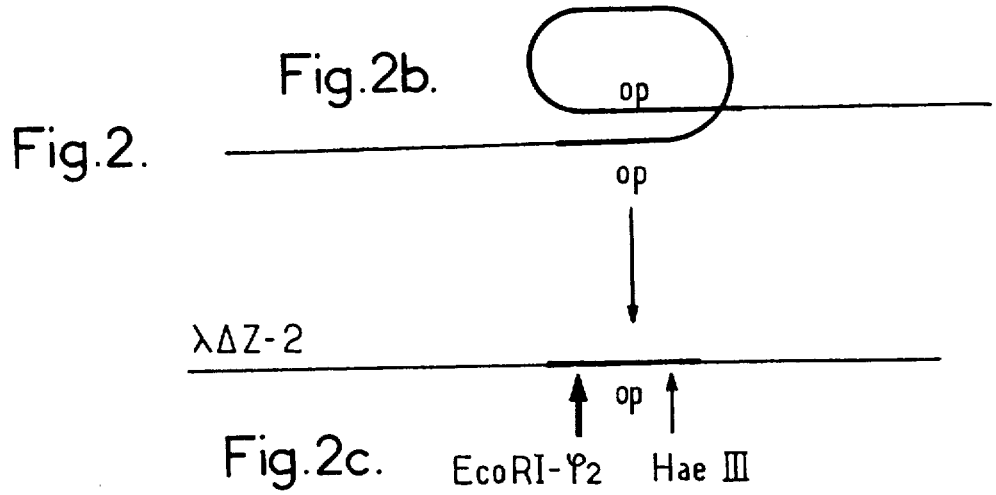

To be certain that the EcoRI ends of the EcoRI 207 fragment have been shifted by two pairs of bases, the nucleotide sequence of the lac Z end of the EcoRI 207 (UV5) fragment was determined. 100 μg of pOP203, pPC21 and pPC22 plasmids were digested with EcoRI endonuclease. To follow the purification of the DNA fragment, 5 μg of each plasmid were marked at the 5' position with ATP γ 32P and added to the rest of the sample. The DNAs were precipitated by ethanol and the solid residue dissolved in 100 μl of 30 mM sodium acetate. EcoRI 203 (UV5) and EcoRI 207 (UV5) fragments were purified by electrophoresis in an 8% polyacrylamide gel. After elution of the gel, the DNAs were marked with ATP γ 32P having a high specific activity. After digestion with HpaII endonuclease, the shortest radioactive DNA fragment, which corresponded to the end of the lac Z gene was purified by electrophoresis in an 8% polyacrylamide gel. The nucleotide sequence of these DNA fragments was done according to the method of Maxam and Gilbert. As anticipated, the sequence of pPC21 and pPC22 plasmids showed that two pairs of GC bases had been inserted immediately before the EcoRI restriction site, and hence that the lac Z end of the two EcoRI 207 (UV5) fragments possessed the translation phase which was the Φ2 phase defined previously (FIG. 2).

Construction of the DNA EcoRI 211 (UV5) Fragment and verification of its structure The DNA EcoRI 211 (UV5) fragment has two pairs of supplementary bases at each end with respect to the EcoRI 207 (UV5) fragment. This DNA fragment was obtained from the EcoRI 207 (UV5) fragment by a series of steps identical to those which provided the DNA EcoRI 207 (UV5) fragment from the EcoRI 203 (UV5) fragment. The nucleotide sequence of the lac Z end of the EcoRI 211 (UV5) fragment was determined from three plasmids (pPC31, pPC32 and pPC33). The EcoRI end has four pairs of GC bases supplementary with respect to the initial EcoRI 203 (UV5) fragment and corresponded to the Φ3 (FIG. 2) phase.

Construction of the bacteriophages λΔZ1, λΔZ2 (phase Φ2) and λΔZ3 (phase Φ3)

The λΔZ1 bacteriophage was produced as follows from λΔZQS-EcoRI bacteriophage deposited under No. I-055 at the C.N.C.M.

The λΔZ1 phage is distinguished from the preceding one essentially by a deletion under the conditions described below by means of the illustrative diagrams of FIGS. 4a to 4d.

Starting from the λΔZQS-EcoRI phage, the OP Hae III 203 (Diagram 4a) fragment, bearing two EcoRI ends, was inserted in the EcoRI-Z site (by the techique described by Backman, K. et Coll., Proc. Nat. Acad. Sci. (1976) 73, pp. 4174–4178). It also includes on each side of the central portion OP, a Z' fragment derived from the beginning of the Z gene and corresponding to the seven first amino-acids codable by the Z gene, and a terminal fragment I" of the repressor of the lactose operon. When the OP Hae III 203 fragment (shown at reduced scale in the diagram 4b) is inserted in the same direction as the homologous OP fragment close to the terminal Z" fragment of the Z gene of the phage (indicated by the reference "op" in the diagram 4b and close to a terminal fragment I" of the gene I of the represser of the lactose operon), an intramolecular recombination creates a deletion (FIG. 4c) of almost the whole of the Z gene. This enables, also, the creation of an EcoRI site (EcoRI-ΔZ site) in place of the Hae III site, very close to the origin of the Z gene at a site corresponding to the seventh amino-acid of β-galactosidase. Finally, of the initial Z gene there only finally subsists the fragments Z" and Z', on both sides of the EcoRI-ΔZ site.

The λΔZ2 bacteriophage was formed like the λΔZ1 (11) bacteriophage, as is indicated in FIG. 2.

(1) In vitro insertion of the EcoRI 207 (UV5) fragment in the EcoRI lac Z site of the genome of λplac5-1 UV5 (FIG. 2a) and (2) intramolecular genetic recombination (shown diagrammatically by FIG. 2b).

The first step gave lac-bacteriophages with the α+ β+ ω− phenotype and the second step gave lac-(α− β− ω−) bacteriophages called λΔZ2. The electrophorectic tracing of the DNA fragments of the λΔZ2 bacteriophage (FIG. 2c) after mixed digestion with EcoRI+HindIII, was identical to the tracing obtained with DNA λΔZ1. This confirmed the intramolecular genetic recombination.

The λΔZ3, λY3 and λY3ZQS bacteriophages were formed in the same manner. λΔZ3 was obtained by in vitro insertion of the EcoRI 211 (UV5) fragment in the restriction site of the λplac5-1, followed by intramolecular genetic recombination. The bacteriophages are shown in FIG. 4.

Construction of the pPCΦ1, pPCΦ2 and pPCΦ3 plasmids

These plasmids were formed to extend the system of three phases to plasmid vectors. The two plasmids were obtained by substitution of the small fragment EcoRI-HindIII of the plasmid pBR322 (C.N.C.M. No. I-065) by the EcoRI-HindIII fragment of the genomes λΔZ1, λΔZ2 and λΔZ3, respectively.

The experimental process was the following: 500 μg of each DNA λΔZ1, λΔZ2 and λΔZ3 were hydrolysed by EcoRI and HindIII enzymes, after mixing with aliquots of 100 μg of pBR322 DNA digested in the same manner. After treatment with the ligase, the three samples of DNA were used to convert the MM294 strain. Blue colonies on the L Xgal ampicillin medium were isolated. For each type of vector, the plasmids of 3 clones were analysed. After digestion with EcoRI and HindIII endonucleases, electrophoretic analysis gave in all cases two DNA bands, one being the EcoRI-HindIII fragment derived from the bacteriophages, the other being the EcoRI-HindIII plasmid fragment. The results are shown for a plasmid of each type, called respectively pPCΦ1, pPCΦ2 and pPCΦ3. To verify that these three plasmids correspond to the three phases, the following analysis was done. The DNA of each of the three plamids was digested with EcoRI endonuclease, the end was dephosphorylated and marked with ATP γ 32P, and finally digested with AluI endonuclease, which cuts the lac promoter very close to the lac Z end. Electrophoretic analysis of the fragment in a 20% polyacrylamide gel showed that it had the expected size. The three plasmids pPCΦ1, pPCΦ2 and pPCΦ3 have a single EcoRI site situated at the beginning of the lac Z gene and enable the insertion of a gene in this site in one of the three phases with respect to the initiation site of translation of the lac Z gene (FIG. 3).

Figure 3:
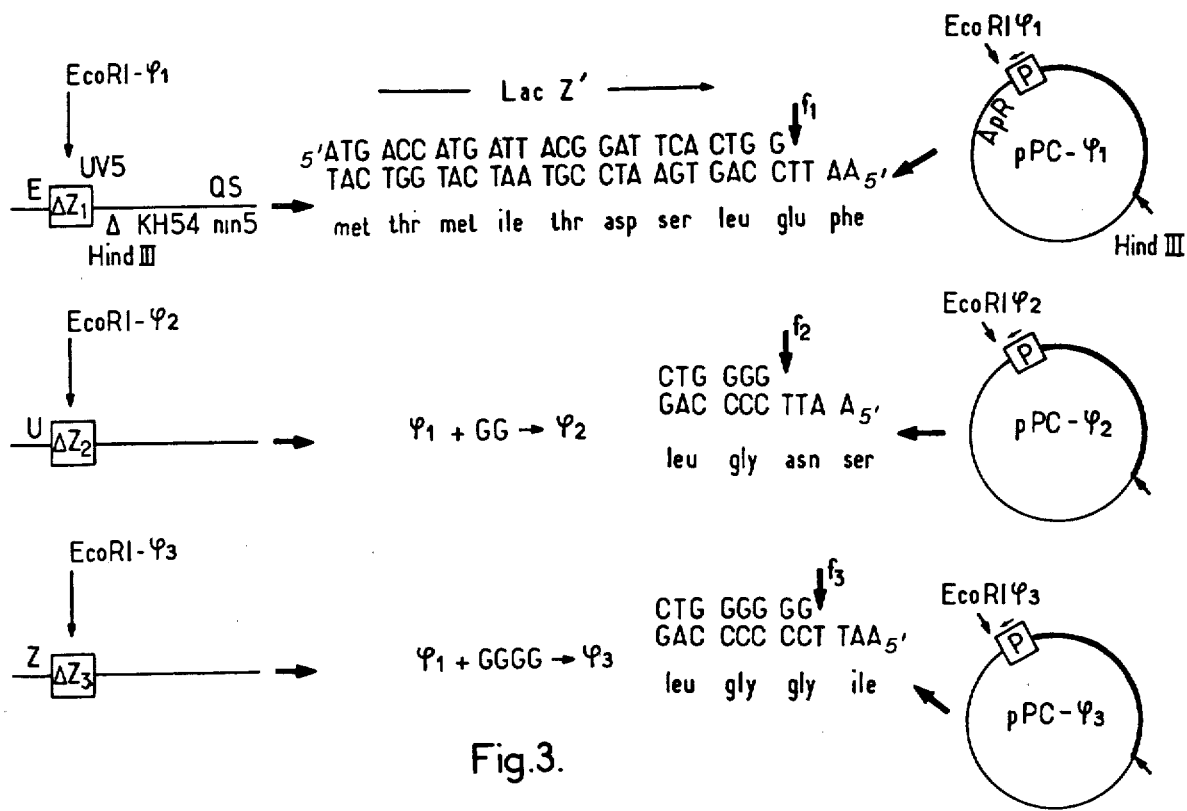
FIG. 3 is a diagram of various vectors of which the invention enables the constitution and finally.

The structures of the vectors, phages or plasmids obtained are briefly recalled in FIG. 3. The lac Z' indication corresponds to the sequence of the gene extending between the initiation site of the translation and the EcoRI site. The addition of two pairs of GC base to this sequence transforms the EcoRI-Φ1 site into an EcoRI-Φ2 site. The further addition of two pairs of supplementary GC bases leads to the EcoRI-Φ3 site. The bacteriophages obtained are shown in the left hand portion of the drawings, the plasmids obtained in the right hand of the drawing.

The arrows f1, f2 and f3 illustrate starting points of the translation of the foreign gene insertable in these vectors.

As is self-evident and as emerges already from the foregoing, the invention is in no way limited to those of its types of applications and embodiments which have been more especially envisaged; it encompasses on the contrary all modifications. Particularly the insertion groups which are at the origin of the shifts concerned are not necessarily provided immediately close to the above-envisaged recognition sites; they could be introduced elsewhere, more particularly in the Z gene fragment, as long as this insertion would not disturb the initiation of the translation of these genes under the effect of the promoter; as has already been indicated, bacterial operons or portions of bacterial operons as other than the lactose operon or portions of lactose operon can be used within the scope of the invention; by way of example, may be mentioned tryptophane, maltose, histidine operons, etc.

BIBLIOGRAPHY

1. Struhl, K., Cameron, J. R. and Davis, R. W. (1976) Proc. Natl. Acad. Sci. U.S.A. 73, 1471–1475.
2. Ratzkin, B. and Carbon, J. (1977) Proc. Natl. Acad. Sci. U.S.A. 74, 487–491.
3. Vapnek, D., Hautala, J. A., Jacobson, J. W., Giles, N. H. and Kushner, S. R. (1977) Proc. Natl. Acad. Sci. U.S.A. 74, 3508–3512.
4. Itakura, K., Hirose, T., Crea, R., Riggs, A. D., Heyneker, H. L., Bolivar, F. and Boyer, H. W. (1977) Science 198, 1056–1063.
5. Villa-Komaroff, L., Efstratiadis, A., Broome, S., Lomedico, P., Tizard, R., Naber, S. P., Chick, W. L. and Gilbert, W. (1978) Proc. Natl. Acad. Sci. U.S.A. 75 No. 8, 3727–3731.
6. Mercereau-Puijalon, O., Royal, A., Cami, B., Garapin, A., Krust, A., Gannon, F. and Kourilsky, Ph. (1978) Nature 275, 505–510.
7. Chow, L. T., Gelinas, R. E., Broker, T. R. and Roberts, R. J. (1977) Cell 12, 1–8.
8. Aloni, Y., Dhar, R., Laub, O., Horowitz, M. and Khoury, G. (1977) Proc. Natl. Acad. Sci. U.S.A. 74, 3686–3690.
9. Marx, J. L. (1977) Science 197, 853–923.
10. Jeffreys, A. J. and Flavell, R. A. (1977) Cell 12, 1097–1108.
12. Tiollais, P., Perricaudet, M., Pettersson, U. and Philipson, L. (1976) Gene 1, 49–63.
13. Barell, B. G. (1971) Proc. in Nucl. Acid. Res. 2, 751–779.
14. Maxam, A. M. and Gilbert, W. (1977) Proc. Natl. Acad. Sci. U.S.A. 74, 560–564.
15. Adams, J. M., Jeppesen, P. G. N., Sanger, F. and Barrel, B. G. (1969) Nature 223, 1009–1014.
16. Sanger, F. and Coulson, A. R. (1975) J. Molec. Biol. 94, 441–448.
17. Bolivar, F., Rodriguez, R. L., Greene, P. J., Betlach, M. C., Heyneker, H. L., Boyer, H. W., Crossa, J. H. and Falkow, S (1977) Gene 2, 95–113.
18. In vitro genetic recombinations. Scientific progress, 191, November–December 1977.
20. Moir, A. and Brammar, W. J. (1976) Molec. Gen. Genet. 149, 87–89.
21. Donoghue, D. J. and Sharp, P. A. (1976) Gene 1, 209–227.

I claim:

1. A composition of matter for the introduction of foreign DNA into a host whereby the expression of a protein having a desired amino acid sequence is provided, said composition of matter comprising the following three structurally interrelated vectors:

(A) a first vector which comprises:
  (i) a preselected bacterial promoter in association with a preselected bacterial gene or part thereof, said preselected bacterial gene or part thereof comprising a translation initiation point,
  (ii) a single recognition site for a preselected restriction endonuclease, said site being in association with the preselected bacterial gene or part thereof, and
  (iii) a plurality of nucleotide base pair triplets between the translation initiation point of the gene or part thereof and the single restriction endonuclease recognition site associated with the gene or part thereof, wherein the plurality of nucleotide base pair triplets does not contain a nonsense codon, and (B) a second vector which comprises
  (i) (A) (i),
  (ii) (A) (ii) and
  (iii) the plurality of nucleotide base pair triplets plus two additional nucleotide base pairs between the translation initiation point of the gene or part thereof and the single restriction endonuclease recognition site associated with the gene or part thereof, wherein the plurality of nucleotide base pair triplets does not contain a nonsense codon, and (C) a third vector which comprises:
  (i) (A) (i),
  (ii) (A) (ii) and
  (iii) the plurality of nucleotide base pair triplets plus 1 or 4 additional nucleotide base pairs between the translation initiation point of the gene or part thereof and the single restriction endonuclease recognition site associated with the gene or part thereof, wherein the plurality of nucleotide base pair triplets does not contain a nonsense codon.

2. The composition of matter as defined in claim 1 wherein the preselected bacterial gene or part thereof is derived from a bacterial operon and the preselected promoter is the promoter associated with the bacterial operon.

3. The composition of matter as defined in claim 2 wherein the single recognition site for the preselected restriction endonuclease is located within the preselected bacterial gene or part thereof or is located in a part of the vector which is adjacent to the end of the gene or part thereof which is farthest from the preselected bacterial promoter.

4. The composition of matter as defined in claim 3 wherein the vector is a phage or a plasmid.

5. The composition of matter as defined in claim 4 wherein the bacterial operon is the lactose operon.

6. The composition of matter as defined in claim 5 wherein the gene or part thereof is the Z gene.

7. The composition of matter as defined in claim 6 wherein the restriction endonuclease is Eco RI.

8. The composition of matter as defined in claim 7 wherein the additional nucleotide base pairs contain bases selected from the group consisting of adenine, thymine, guanine and cytosine.

9. The composition of matter as defined in claim 8 wherein each of the three recited vectors further comprises a preselected foreign DNA fragment which has been inserted into each vector at its single restriction endonuclease recognition site.

10. The composition of matter as defined in claim 9 wherein the host is a bacterium.

11. A bacterial host which has been transformed with the composition of matter as defined in claim 9.

12. A composition of matter for insertion into a preselected vector to make the vector suitable for the introduction of foreign DNA into a host whereby the expression of a protein having a desired amino acid sequence is provided, said composition of matter comprising the following three structurally interrelated DNA insertion fragments:

(A) a first insertion fragment which comprises:
  (i) a preselected bacterial promoter in assocation with at least part of a preselected bacterial gene, said preselected bacterial gene or part thereof comprising a translation initiation point
  (ii) a cohesive end corresponding to a recognition site for a preselected restriction endonuclease, and
  (iii) a plurality of nucleotide base pair triplets between the translation initiation point of the gene or part thereof and the cohesive end corresponding to a recognition site for a preselected restriction endonuclease, wherein the plurality of nucleotide base pair triplets does not contain a nonsense codon, and (B) a second insertion fragment which comprises
  (i) (A) (i),
  (ii) (A) (ii) and
  (iii) the plurality of nucleotide base pair triplets plus two additional nucleotide base pairs between the translation initiation point of the gene or part thereof and the cohesive end corresponding to a recognition site for a preselected restriction endonuclease, wherein the plurality of nucleotide base pair triplets does not contain a nonsense codon, and (C) a third insertion fragment which comprises:
  (i) (A) (i),
  (ii) (A) (ii) and
  (iii) the plurality of nucleotide base pair triplets plus 1 or 4 additional nucleotide base pairs between the translation initiation point of the gene or part thereof and the cohesive end corresponding to a recognition site for a preselected restriction endonuclease, wherein the plurality of nucleotide base pair triplets does not contain a nonsense codon.

13. The composition of matter as defined in claim 12 wherein the preselected bacterial gene or part thereof is derived from a bacterial operon and the preselected promoter is the promoter associated with the bacterial operon.

14. The composition of matter as defined in claim 13 wherein the bacterial operon is the lactose operon.

15. The composition of matter as defined in claim 14 wherein the gene or part thereof is the Z gene.

16. The composition of matter as defined in claim 15 wherein the restriction endonuclease is Eco RI.

17. The composition of matter as defined in claim 16 wherein the additional nucleotide base pairs contain bases selected from the group consisting of adenine, thymine, guanine, and cytosine.

18. The composition of matter as defined in claim 17 wherein the host is a bacterium.

19. Composition of matter for the introduction of foreign DNA into a host whereby the expression of a protein having a desired amino acid sequence is provided, said composition of matter comprising the following three structurally interrelated vectors:

(A) a first vector which comprises:
  (i) a promoter and gene associated therewith in a preselected bacterial operon or part of said gene,
  (ii) a single recognition site for a preselected restriction endonuclease associated with said gene or part of gene and
  (iii) a number of nucleotide base pairs between the reading initiation point of the gene and the single restriction endonuclease recognition site associated with said gene (B) a second vector which comprises:

(i) The promoter and gene or part of gene of said first vector, (ii) the single recognition site of said first vector, and (iii) the number of nucleotide base pairs of said first vector plus two additional nucleotide base pairs and, optionally, a whole number of supplementary triplets between said reading initiation point and said single restriction endonuclease recognition site, wherein the bases of said additional nucleotide base pairs and said optional supplementary triplets are selected such as to exclude those which, in the order in which they are placed with respect to said initiation point, would form at least one nonsense codon, (C) a third vector which comprises:

(i) the promoter and gene or part of gene of said first vector, (ii) the single recognition site of said first vector, and (iii) the number of nucleotide base pairs of said first vector, plus one or four additional nucleotide base pairs and, optionally, a whole number of supplementary triplets between said reading initiation point and said single restriction endonuclease recognition site, wherein the bases of said one or four additional nucleotide base pairs and said optional supplementary triplets are selected such as to exclude those which, in the order in which they are placed with respect to said reading initiation point, would form at least one nonsense codon.

20. The composition of claim 19 wherein the bacterial operon is the lactose operon and the gene or part thereof is the Z gene or a part thereof.

21. The composition of claim 20 wherein the restriction site is a EcoRI site.

22. A composition of matter for insertion into a preselected vector to make the vector suitable for the introduction of foreign DNA into a host, whereby the expression of a protein having a desired amino acid sequence is provided, said composition of matter comprising the following three structurally interrelated DNA insertion fragments:

(A) a first insertion fragment which comprises:

(i) a promoter and gene associated therewith in a preselected bacterial operon or part of said gene, (ii) a single recognition site for a preselected restriction endonuclease associated within said gene or part of gene and (iii) a number of nucleotide base pairs between the reading initiation point of the gene and the single restriction endonuclease recognition site associated with said gene (B) a second insertion fragment which comprises:

(i) the promoter and gene or part of gene of said first insertion fragment, (ii) the single recognition site of said first insertion fragment, and (iii) the number of nucleotide base pairs of said first insertion fragment plus two additional nucleotide base pairs and, optionally, a whole number of supplementary triplets between said reading initiation point and said single restriction endonuclease recognition site, wherein the bases of said additional nucleotide base pairs and said optional supplementary triplets are selected such as to exclude those which, in the order in which they are placed with respect to said initiation point, would form at least one nonsense codon, (C) a third insertion fragment which comprises:

(i) the promoter and gene or part of said first insertion fragment, (ii) the single recognition site of said first insertion fragment, and (iii) the number of nucleotide base pairs of said first insertion fragment, plus one or four additional nucleotide base pairs and, optionally, a whole number of supplementary triplets between said reading initiation point and said single restriction endonuclease recognition site, wherein the bases of said one or four additional nucleotide base pairs and said optional supplementary triplets are selected such as to exclude those which, in the order in which they are placed with respect to said reading initiation point, would form at least one nonsense codon.

23. The composition of claim 22 wherein the bacterial operon is the lactose operon and the gene or part of said gene is the Z gene or a part thereof.

24. The composition of claim 23 wherein the restriction site is an EcoRI site.

* * * * *